United States Patent [19]

Kawada et al.

[11] Patent Number: 5,702,928
[45] Date of Patent: Dec. 30, 1997

[54] PROCESS FOR PRODUCING OPTICALLY ACTIVE TRIAZOLE COMPOUNDS AND METHOD OF RACEMIZING OPTICALLY ACTIVE TRIAZOLE COMPOUNDS

[75] Inventors: Naoki Kawada; Noritsugu Yamazaki; Takafumi Imoto; Kiyoshi Ikura, all of Ibaraki, Japan

[73] Assignee: Daicel Chemical Industries, Ltd., Japan

[21] Appl. No.: 617,747

[22] PCT Filed: Jul. 17, 1995

[86] PCT No.: PCT/JP95/01416

§ 371 Date: May 24, 1996

§ 102(e) Date: May 24, 1996

[87] PCT Pub. No.: WO96/02664

PCT Pub. Date: Feb. 1, 1996

[30] Foreign Application Priority Data

Jul. 18, 1994 [JP] Japan .................... 6-165281
Aug. 9, 1994 [JP] Japan .................... 6-187032

[51] Int. Cl.[6] ............ C12P 17/10; C07D 249/08
[52] U.S. Cl. ............ 435/121; 548/255; 548/269.2
[58] Field of Search .................. 548/269.2, 255; 435/121

[56] References Cited

FOREIGN PATENT DOCUMENTS

| 0472392A2 | 2/1992 | European Pat. Off. |
| 0539938A1 | 5/1993 | European Pat. Off. |
| WO 88/05048 | 7/1988 | WIPO |
| WO 94/24305 | 10/1994 | WIPO |

OTHER PUBLICATIONS

Lovey, Raymond G. et al., Tetrahedron Letters, vol. 35, No. 33, pp. 6047–6050 (1994) (Aug. 15, 1994).

Blundell, Paul et al., Synlett, Apr./94, pp. 263–265.

*Primary Examiner*—Johann Richter
*Assistant Examiner*—Jane C. Oswecki
*Attorney, Agent, or Firm*—Fish & Richardson P.C.

[57] ABSTRACT

A process for the asymmetric synthesis of a compound represented by general formula (II-R) easily at a low cost by using a lipase, and a process for producing a compound to be utilized in the above synthesis.

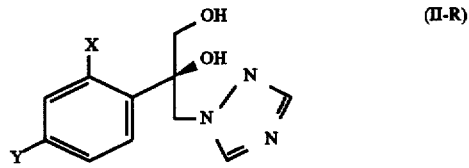

31 Claims, No Drawings

PROCESS FOR PRODUCING OPTICALLY ACTIVE TRIAZOLE COMPOUNDS AND METHOD OF RACEMIZING OPTICALLY ACTIVE TRIAZOLE COMPOUNDS

This application is a 371 of PCT/JP95/01416 of Jul. 17, 1995.

FIELD OF THE INVENTION

The present invention relates to a process for producing a compound having the formula (II-R). In addition, the present invention relates to a process for producing a compound having the formula (I-R). Furthermore, the present invention relates to a method for racemizing a compound having the formula, (I-R), (I-S), (II-R) or (II-S), and leading to a compound having the formula (II) with the optical activity reduced or eliminated. Of compounds having the formula (II-R), particularly, R(-)-2-(2,4-difluorophenyl)-3-(1H-1,2,4-triazol-1-yl) propane-1,2-diol is important as the intermediate for synthesizing medicines such as anti-fungal agents.

In the present invention, the formulas (I), (II), (I-R), (I-S), (II-R), or (II-S) stand for the compounds of the following structures, respectively.

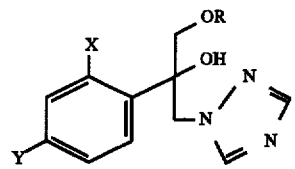

(I)

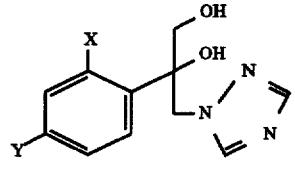

(II)

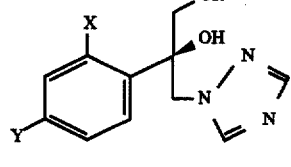

(I-R)

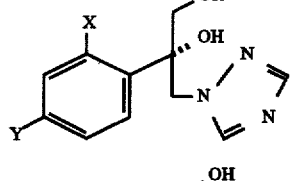

(I-S)

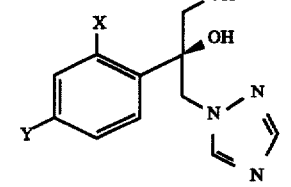

(II-R)

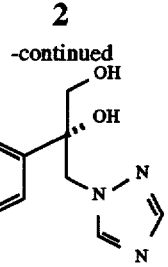

(II-S)

In this specification, the formulas (I) and (II) represent not only racemates, comprising both diastereoisomers in the same ratio, but also a mixture comprising both isomers in a different ratio, one of the isomers in a higher ratio than that of the other. Also the formulas (I-R), (I-S), (II-R) or (II-S) represent the compound wherein the content of either the R-isomer or the S-isomer is higher than the other, regardless of their optical purity.

BACKGROUND OF THE INVENTION

The conventional methods for preparing R-(-)-2-(2,4-difluorophenyl)-3-(1H-1,2,4-triazol-1-yl)propane-1,2-diol comprise:

1) asymmetric oxidation of 2-(2,4-difluorophenyl) allylalcohol with t-butyl hydroperoxide in the presence of titanium tetraisopropoxide and diethyl L(+)-tartrate to first synthesize S-(-)-2-(2,4-difluorophenyl)-2,3-epoxypropanol, which is then reacted with 1,2,4-triazole in the presence of potassium carbonate or the like to obtain R-(-)-2,(2,4-difluorophenyl)-3-(1H-1,2,4-triazole-1-yl)propane-1,2-diol (see the specifications in TokkaiHei 5-91183 and Eur. Patent 539938), and 2) hydrolysis of 1-acetoxy-2-(2,4-difluorophenyl)-2,3-epoxypropane with a hydrolase to produce R-(-)-1-acetoxy-2-(2,4-difluorophenyl)-2,3-epoxypropane, which is converted, first by the ester hydrolytic reaction, to S-(-)-2-(2,4-difluorophenyl) -2,3-epoxypropanol, and then led to R-(-)-2-(2,4-difluorophenyl)-3-(1H-1,2,4-triazol-1-yl) propane-1,2-diol in the presence of potassium carbonate as in the previous method (see TokkaiHei 5-91183).

However, method 1) comprises complicated procedures and method 2 offers a poor yield.

Another conventional method for racemizing optically active alcohol comprises the acetylation or tosylation of the optically active secondary alcohol, followed by reaction with acetic acid in the presence of a strong acid to give racemic acetic acid ester, which is deacetylated to give racemic alcohol (1)(Journal of American Chemical Society, 87, p.3682 (1965), (2) Journal of Chemical Society, p.965 (1954), (3) Journal of Chemical Society, p.840 (1939). The procedure in the above method is not simple, because it comprises the conversion of a hydroxyl group linked to the asymmetric carbon to a carboxylic acid ester, followed by the racemization and then hydrolysis of said ester. Furthermore, there is no indication of a method for directly racemizing a tertiary alcohol having a hydroxyl or acyloxy group on the adjacent carbon.

The present invention aims to provide a method for preparing a compound represented by the formula (II-R) with high optical purity using an economical and simple means. The present invention also aims to provide a method for preparing a compound represented by the formula (I-R). Furthermore, the present invention aims to provide a method for producing a compound having the formula (II) with the optical activity reduced or nullified by racemizing a compound having the formula (I-R), (I-S), (II-R) or (II-S) by convenient means.

DISCLOSURE OF THE INVENTION

During developmental studies on an economic and convenient method for preparing a compound having the formula (II-R) with high optical purity, we found that lipase, especially microbial lipase, is highly capable of catalyzing the asymmetric ester interchange reaction with a compound having the formula (II), and also that compounds having the formulas (II-R) and (I-S), or the formulas (II-S) and (I-R) could be synthesized by reacting $R_1COOR_2$ (wherein $R_1$ is a straight or branched $C_1$–$C_4$ alkyl or alkenyl group, and $R_2$ is a straight or branched $C_1$–$C_6$ alkyl or alkenyl group) and a compound having the formula (II) in the presence of lipase. We also found that a lipase, especially lipase of microbial origin, synthesized a compound having the formula (I) from a compound having the formula (II), and also an asymmetrically hydrolyzed compound having the formula (I), with high efficiency to produce compounds having the formulas (II-R) and (I-S), or compounds having the formulas (I-S) and (I-R).

The present invention provides a novel method for producing a compound having the formula (II-R). In addition, the present invention provides a method for producing a compound having the formula (I-R).

Furthermore, during careful studies on a method for racemizing an optically active compound having the formula (I-R), (I-S), (II-R) or (II-S), we also found that an optically active compound having the formula (I-R), (I-S), (II-R) or (II-S) can be racemized to form a compound having the formula (II) by the treatment of said compound with a strong acid in the case of a compound having the formula (II-R) or (II-S), the addition of acylating agent is required, followed by deacylation.

The present invention provides a method for producing a compound having the formula (II) with the optical activity reduced or nullified by racemizing a compound having the formula (I-R), (I-S), (II-R) or (II-S) using a simple means.

Method for Producing Compound Having the Formula (II-R)

In the present invention, for the production of a compound having the formula (II-R), either one of the following two methods can be applied:

1) Acylation of a compound having the formula (II) (Reaction I), or
2) Hydrolysis of a compound having the formula (I) (Reaction III).

Reaction I

The compound having the formula (II) which is used in Reaction I can be prepared by the conventional method (see TokkaiHei 5-9183).

The compound having the formula (II-R) can be synthesized from a compound having the formula (II) by reacting a compound having the formula (II) with $R_1COOR_2$ in the presence of lipase, wherein $R_1$ is a straight or branched $C_1$ to $C_4$ alkyl or alkenyl group, for example a methyl, ethyl, propyl, butyl, isopropyl, isopropenyl, vinyl, allyl or propenyl group. $R_2$ is a straight or branched $C_1$ to $C_6$ alkyl or alkenyl group, for example a methyl, ethyl, isopropyl, vinyl, allyl or hexyl group.

Any lipase suitable for achieving the present purpose may be used in Reaction I. However, preferably, lipase derived from a microorganism of the genus Mucor, Candida, Penicillium, Pseudomonas or Rhizopus may be used. Preferable examples are lipases produced by *Mucor javanicus, Candida cylindracea, Penicillium cyclobium, Pseudomonas sp., Rhizopus delemar, Pseudomonas fragi, Mucor miehei* or *Pseudomonas cepacia* These lipases can be obtained by culturing microorganisms producing said lipases or extracting them from animal tissues, and may be used in any form conventionally used, for example, in the form of the microbial culture medium, crude enzyme, or purified enzyme. Furthermore, lipases derived from some microorganisms are commercially available under the following trade names and can be used: Lipase M (from *Mucor javanicus*, Amanoseiyaku), Lipase AY (from *Candida cylindracea*, Amanoseiyaku)), Penicillin Lipase C (from *Penicillium cyclobium*, Cosmobio), Lipase P (from *Pseudomonas sp.*, Nagase Seikagakukogyo), Lipase (from *Rhizopus delemar*, Seikagakukogyo), Lipase SE-B (from *Pseudomonas fragi*, Funakosi), and Lipozyme ZM60 (from *Mucor miehei*, Novo). Lipases may be used singly or in a combination thereof. Also they may be used in an immobilized enzyme form prepared by the conventional method.

Reaction I may be performed by the catalytic action of said lipase on a compound having the formula (II) with a compound having the formula $R_1COOR_2$ added thereto in an organic solvent. The Molar ratio of the compound having the formula $R_1COOR_2$ to the compound having the formula (II) is usually higher than 0.6, preferably higher than 0.9. The compound having the formula $R_1COOR_2$ may be contained in large excess in the reaction mixture. $R_1COOR_2$ may be used as the solvent, serving as the substrate for the reaction at the same time. In this reaction, the addition of any other solvent may not necessarily be required, but, if necessary, a suitable solvent such as n-hexane may be added. The concentration of the compound having the formula (II), substrate, is usually 0.1 to 50%, preferably 0.5 to 30%. Reaction temperature may vary with the enzyme used, and is usually in the range of 10° to 60° C., preferably in the range of 20° to 50° C. The enzyme concentration in the reaction mixture may be determined according to the specific activity of the respective enzyme preparation, and exemplified by 1 to 10 weight percent. The reaction may be performed either with stirring or by being allowed to stand, preferably with stirring. After the reaction, the enzyme may be recovered by centrifuging or filtering the reaction mixture, and re-used.

In Reaction I, the compound having the formula (I-S) is also produced at the same time. We found that the compound having the formula (I-S) could be racemized to form a compound having the formula (II) by treatment with a strong acid followed by deacylation.

Strong acids used in said racemizing reaction are exemplified by inorganic acids such as sulfuric acid, perchloric acid, phosphoric acid and hydrochloric acid, alkyl sulfates such as methanesulfonic acid and trifluoromethanesulfonic acid, and aromatic sulfates such as toluenesulfonic acid and benzenesulfonic acid, preferably an aromatic sulfuric acid or sulfuric acid, more preferably sulfuric acid. The amount of acid used varies depending upon the reaction temperature and stability of the substrate, and is not restricted to any amount, but it is usually in the range of 10 to 1,000 weight parts for 100 weight parts of substrate, preferably in the range of 50 to 400 weight parts.

For smooth operation of said racemization reaction, it is usually preferable to perform the reaction in the presence of an acylating agent. Preferred acylating agents comprise aliphatic carboxylic acid esters such as methyl acetate, ethyl acetate, butyl acetate, propyl acetate, isopropyl propionate and methyl butylate; aromatic carboxylic acid esters such as methyl benzoate and propyl benzoate; aliphatic carboxylic acids such as formic acid, acetic acid, propionic acid, isopropionic acid, butyric acid, valeric acid, trichloroacetic acid and trifluoroacetic acid; aromatic carboxylic acids such as benzoic acid and substituted benzoic acid; aralkyl carboxylic acids such as phenylacetic acid, phenylpropionic acid and phenylbutyric acid; acid anhydrides such as acetic anhydride, propionic anhydride, butyric anhydride, valeric anhydride and benzoic anhydride; or a mixture of carboxylic acid and water. For ease of separation after the reaction and reactivity, aliphatic carboxylic acids such as formic acid, acetic acid, propionic acid, and butyric acid or a mixture of said acid and water are especially preferred. The amount of acylating agent to be used varies depending upon the reaction temperature, and is not restricted to any amount. However, it is usually in the range of 30 to 400 weight parts for 100 weight parts of the substrate, preferably in the range of 100 to 1000 weight parts. Reaction temperature is also not restricted to any temperature, but the reaction is usually carried out at 0° to 150° C., preferably in the range of 20° to 100° C. Although a reaction solvent is not necessarily required, the reaction may be carried out under conditions wherein the reaction solution is diluted with inert solvent.

At the stage of treating the compound having said formula (I) with a strong acid, the optical activity of the compound having the formula (I) or (II) is reduced. Although the compound obtained at this stage is not necessarily a single compound, depending on reaction conditions and differences in the type of starting material, by the succeeding deacylation reaction, said compound eventually is unified to become compound having the formula (II) with the optical activity reduced or eliminated.

The deacylation reaction may be carried out by treating the compound with acid or base in water, alcohol or diluted alcohol. The term alcohol as used herein means alcohol used for alcoholysis of ester, but does not limit the type of alcohol. However, for ease of purification of the alcohol, low alcohols with low boiling points such as methanol, ethanol, propanol, isopropanol and butanol are preferred. The mixing ratio between water and alcohol is not essential. In addition, alcohol may be diluted with a solvent inert to the reaction. Reaction temperature and reaction time may also vary with the type of acid or base used, but the reaction is usually carried out at a temperature in the range of 20° to 100° C. The acid to be used may be exemplified by sulfuric acid, hydrochloric acid and p-toluenesulfonic acid. Preferably these acids are used in more than a gram equivalent amount with the usual substrate. The base to be used may be exemplified by lithium hydroxide, sodium hydroxide, potassium hydroxide, magnesium hydroxide, sodium carbonate and sodium bicarbonate. Preferably these bases are used in more than a gram equivalent amount with the usual substrate.

A compound having the formula (II) may be converted to a compound having the formula (II-R) by the action of lipase, again according to Reaction I. That is, a compound having the formula (I-S) may be used for the synthesis of a compound having the formula (II-R).

Reaction III

A compound having the formula (I) used in Reaction III can be synthesized by treating a compound having the formula (II) with acid anhydride or acid chloride in the presence of an acid or base. For the synthesis of a compound having the formula (II-R) from a compound having the formula (I), any lipase suitable for the purpose may be used, preferably lipases derived from microorganisms belonging to the genus Penicillium or Candida are used. Preferable examples are lipases produced by *Penicillium roquefortii* and *Candida cylindracea*. These lipases can be obtained by culturing said microorganism producing said enzyme. Said enzyme can be used in any form such as that commonly used, for example, in bacterial culture medium, as a crude enzyme or purified enzyme. Commercially available lipase (s) may also be used, for example, Penicillin lipase R (Cosmo-Bio) derived from *Penicillium roquefortii*, and lipase OF (Meito Sangyo) derived from *Candida cylindracea*. Lipases may be used singly or in a combination thereof, if necessary. These enzymes can be used in forms immobilized on a proper support prepared by a usual method. The concentration of the compound having the formula (I), the substrate, is usually 0.1 to 50%, preferably 0.5 to 30%. The reaction temperature is dependent on the type of enzyme to be used. The Reaction is carried out usually at a temperature in the range of 10° to 60° C., preferably 20° to 50° C. The concentration of enzyme in the reaction solution may be selected depending upon the specific activity of the respective enzyme preparation, for example, 0.1 to 10 weight percent. The pH of the reaction solution may be adjusted to within the range of 4 to 10, preferably to the optimal pH of the enzyme to be used. For this adjustment, a suitable buffer may be used, or the reaction may be performed while controlling pH with a sodium hydroxide or potassium hydroxide solution using a pH star. The reaction may be performed with or without stirring, preferably while stirring. After the completion of the reaction, the enzyme may be separated from the reaction solution by centrifugation or filtration, and re-used.

In Reaction III, a compound having the formula (I-S) is concomitantly produced. As described in detail in Reaction I, a compound having the formula (I-S) can be racemized to form a compound having the formula (II) by treating (I-S) with a strong acid followed by deacylation. A compound having the formula (II) can be converted to a compound having the formula (II-R) by treating said compound again with lipase according to Reaction I. That is, a compound having the formula (I-S) may be used for the synthesis of a compound having the formula (II-R).

<Preparation of Compound Having the Formula (I-R)>

A compound having the formula (II-R) may also be synthesized by treating a compound having the formula (II) or (I) first with lipase to produce a compound having the formula (I-R), which is then chemically converted to a compound having the formula (II-R). Conversion of a compound having the formula (I-R) to a compound having the formula (II-R) can be readily performed by the usual hydrolysis of ester catalyzed by acid or alkali. A preffered acidic catalyst is diluted hydrochloric acid, and a preferred basic catalyst is potassium hydroxide or sodium hydroxide.

For preparing a compound having the formula (I-R), either one of the following two methods may be used:

1) method for acylating a compound having the formula (II) (Reaction II), or 2) method for hydrolyzing a compound having the formula (I) (Reaction IV).

Reaction II

For synthesizing a compound having the formula (I-R) from a compound having the formula (II) according to Reaction II, the compound having the formula (II) is treated with $R_1COOR_2$ in the presence of lipase, wherein $R_1$ is a $C_1$ to $C_4$ straight or branched alkyl or alkenyl group, such as a methyl, ethyl, propyl, butyl, isopropyl, isopropenyl, vinyl, allyl or propenyl group, and $R_2$ is a straight or branched $C_1$ to $C_6$ alkyl or alkenyl group, such as a methyl, ethyl, isopropyl, vinyl, allyl or hexyl group.

In Reaction II, any lipase suitable for carrying out the purpose may be used; preferably a lipase produced by the genus Geotrichum is used. A preferred embodiment is exemplified by the lipase produced by *Geotrichum candidum*. These lipases may be obtained by culturing microorganisms producing said enzymes, and may be used in any form routinely used, for example, in the form used for bacterial culture medium, as a crude enzyme or purified enzyme. The lipase derived from *Geotricum candidum* is commercially available under the trade name, *Diotricium candidum* Lipase (Cosmobio), and can be used as such. Lipases may be used singly or in a combination thereof. These enzymes may be used in an immobilized form by fixing them to a suitable solid support by the conventional method.

Reaction II may be performed by treating a compound having the formula (II) and a compound having said formula $R_1COOR_2$ added thereto with said lipase in an organic solvent. The molar ratio of the compound having the formula $R_1COOR_2$ to the compound having the formula (II) is usually higher than 0.6, preferably higher than 0.9. The compound having the formula $R_1COOR_2$ may be used in large excess, and used as a solvent, while serving as a substrate at the same time. Addition of another solvent is not necessarily required for carrying out the reaction, but a suitable organic solvent such as n-hexane may be added. The concentration of the compound having the formula (II), the substrate, is usually 0.1 to 50%, preferably 0.5 to 30%. The reaction temperature depends on the type of enzyme to be used. The reaction is usually performed at a temperature in the range of 10° to 60° C., preferably 20° to 50° C. The concentration of the enzyme in the reaction solution may be selected based on the specific activity, and may be exemplified by the range of 0.1 to 10 weight percent. The reaction may be carried out with or without stirring, and preferably while stirring. After the completion of the reaction, the enzyme may be separated by a centrifugation or filtration procedure, and re-used.

In Reaction II, a compound having the formula (IFS) is concomitantly produced. Since the compound having the formula (IFS) can be racemized to form a compound having the formula (II), which will be converted to a compound having the formula (II-R) by the action of lipase, again according to Reaction II, the compound having the formula (II-S) may be used for the synthesis of a compound having the formula (II-R). The method of racemization is exemplified by the following two methods.

In one of the methods, a compound having the formula (II-S) is first converted, by an treatment with acid anhydride or acid chloride in the presence of an acid or base, to a compound having the formula (I-S), from which a compound having the formula (II) is produced by the method described in detail for said Reaction I.

However, we found a method for producing a racemate having the formula (II), wherein an optically active compound having the formula (I) or (II) is treated with a strong acid and acylating agent, and then deacylated.

Strong acids as used herein are exemplified by inorganic acids such as sulfuric acid, perchloric add, phosphoric acid and hydrochloric acid; alkylsulfonic acids such as methane sulfonate and trifluoromethanesulfonic acid; and aromatic sulfonic acids such as toluenesulfonic acid and benzenesulfonic acid; preferably aromatic sulfonic acid or sulfuric acid, and, more preferably, sulfuric acid. The concentration of acid to be used depends on the reaction temperature and substrate stability, and is not restricted to any concentration, but is usually in the range of 10 to 1,000 weight parts for 100 weight parts of substrate, preferably in the range of 50 to 400 weight parts.

Preferable acylating agents as used herein comprise aliphatic carboxylic acid esters, including methyl acetate, ethyl acetate, butyl acetate, propyl acetate isopropyl propionate and methyl butyrate; or aromatic carboxylic acid esters such as methyl benzoate and propyl benzoate; or aliphatic carboxylic acids, including formic acid, acetic acid, propionic acid, isopropionic acid, butyric acid, valeric acid, trichloroacetic acid and trifluoroacetic acid; or aromatic carboxylic acid such as benzoic acid and substituted benzoic acid; or aralkyl carboxylic acid such as phenylacetic acid, phenylpropionic acid and phenylbutyric acid; or acid anhydrides, including acetic anhydride, propionic anhydride, butyric anhydride, valeric anhydride and benzoic anhydride; or a mixture of carboxylic acid and water. For ease of separation after the reaction and reactivity, aliphatic carboxylic acids, including formic acid, acetic acid, propionic acid and butyric acid, or a mixture of the respective acid and water are most preferable. The amount of acylating agent to be used depends on the reaction temperature, is not restricted to any amount, and is usually in the range of 30 to 400 weight parts for 100 weight parts of substrate, preferably in the range of 100 to 1,000 weight parts. The reaction temperature is also not restricted to any temperature, and the reaction is usually performed at a temperature in the range of 0° to 150° C., preferably in the range of 20° to 100° C. A reaction solvent is not necessarily required, but the reaction may be performed under diluted conditions by the addition of a solvent inert to the reaction, if necessary.

At the stage of treating a compound having the formula (II) with a strong acid and acylating agent, the optical activity of the compound having the formula (I) or (II) is reduced. Although the compound obtained at this stage is not necessarily a single compound, depending on reaction conditions or the type of starting material, by the succeeding deacylating reaction, said compound will be eventually unified to become a compound having the formula (II) with the optical activity reduced or eliminated.

The deacylating reaction may be carried out by treating the compound with an acid or base in water, alcohol or diluted alcohol. The term alcohol as used herein means alcohol to be used for alcoholysis of an ester, and is not restricted to any type. However, for ease of purification of the product, low alcohols with low boiling points such as methanol, ethanol, propanol, isopropanol and butanol are preferred. The mixing ratio of water and alcohol is not essential, and the alcohol may be diluted with a solvent inert to the reaction. In addition, the reaction temperature and reaction time depend on the type of acid or base, and not restricted specifically, and the reaction is usually carried out at a temperature in the range of 20° to 100° C. An acid to be used is exemplified by sulfuric acid, hydrochloric acid and p-toluenesulfonic acid, and preferably is used in more than a gram equivalent amount. A base to be used is exemplified by lithium hydroxide, sodium hydroxide, potassium hydroxide, magnesium hydroxide, sodium carbonate and sodium bicarbonate, and preferably used in more than a gram equivalent amount.

Reaction IV

A compound having the formula (I) used in Reaction IV can be synthesized by reacting a compound having the formula (II) with an acid anhydride or acid chloride in the presence of an acid or base. Although any type of lipase may be used for synthesizing a compound having the formula (I-R) from a compound having the formula (I), so far as said lipase is suitable for carrying out the purpose of the invention, preferably a lipase produced by microorganisms belonging to the genus Mucor, Penicillium, Chromobacterium, Rhizopus, Pseudomonas or Alcaligenes may be used. As a preferred embodiment, lipases produced by *Mucor javanicus, Penicillium cyclobium, Chromobacterium viscosum, Rhizopus japonicus, Rhizopus delemar, Pseudomonas sp., Alcaligenes sp.* or *Pseudomonas cepacia* may be used. These lipases may be obtained by culturing microorganisms producing said enzymes, and utilized in any form used routinely, for example, in the form used for bacterial culture medium, as a crude enzyme or purified enzyme. Furthermore, several lipases derived from bacteria are commercially available under the following trade names for experimental use: Lipase M from *Mucor javanicus* (Amano seiyaku), Penicillin lipase C from *Pencillium cyclobium* (Amanoseiyaku), Lipase from *Chromobacterium viscosum* (Asahi Kasei), Rhilipase from *Rhizopus japonicus* (Nagase-Seikagakukogyo), Talipase from *Rhizopus delemar* (Tanabe), Lipase P from *Pseudomonas sp.* (Nagase-Seikagakukogyo) and Lipase PL from *Alcaligenes sp.* (Meito Sangyo). Lipases may be used singly or in combination, if necessary. These enzymes may be used in an immobilized form fixed on a solid support by the conventional method. The concentration of a compound having the formula (I), the substrate, is usually 0.1 to 50%, preferably 0.5 to 30%. The reaction temperature depends on the type of enzyme to be used. The reaction is usually performed at a temperature in the range of 10° to 60° C., preferably 20° to 50° C. The enzyme concentration in the reaction mixture may be determined depending on the specific activity of the respective enzyme preparation, and may be exemplified by a concentration of 0.1 to 10 weight percentage. The pH of the reaction solution may be in the range of 4 to 10, preferably adjusted to the enzyme's optimal pH. For this pH adjustment, a suitable buffer may be employed, or the pH of the reaction solution may be controlled with a pH stat using a sodium hydroxide or potassium hydroxide solution. The reaction may be performed with or without stirring, preferably with stirring. After the reaction is completed, the enzyme may be separated by centrifugation or filtration and re-used.

In Reaction IV, a compound having the formula (II-S) is concomitantly produced. Since a compound having the formula (II-S) can be racemized to form a compound having the formula (II), which is converted to a compound having the formula (II-R) by the action of lipase, compound having the formula (II-S) can be used for synthesis of a compound having the formula (II-R). For racemization, said method described in detail in Reaction II may be used.

MOST PREFERRED EMBODIMENT FOR PREFORMING THE INVENTION

In the following section, preferred embodiments illustrate the present invention. However, the present invention is not restricted to the example presented here.

Citation 1 Synthesis of racemic 1-acetoxy-2-(2,4-difluorophenyl)-3-(1H-1,2,4-triazol-1-yl)propane-2-ol (abbreviated as AcFTAP hereinafter, formula III) from racemic 2-(2,4-difluorophenyl)-3-(1H-1,2,4-triazol-1-yl)propane-1,2-diol (abbreviated as FTAP hereinafter, formula IV) (Method 1)

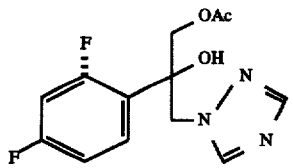
(III)

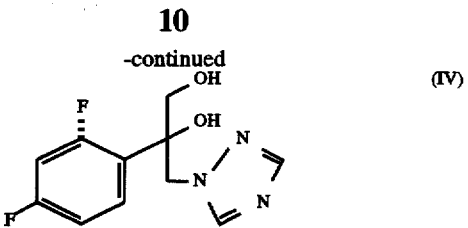
(IV)

To a solution of FTAP (5.00 g, 19.6 mmol) in tetrahydrofuran (15 ml) were added pyridine (2.8 ml, 39.0 mmol) and acetic anhydride (2.8 ml, 29.7 mmol), and the mixture was stirred at room temperature for 15 h. After the reaction solution was basified with sodium hydroxide solution, the mixture was extracted with ethyl acetate (80 ml) three times. After the solvent was evaporated in vacuo, the residue thus obtained was purified by silica gel column chromatography to give AcFTAP (5.17 g, 17.4 mmol, 89%).

Citation 2 Synthesis of Racemic AcFTAP from Racemic FTAP (Method 2)

To FTAP (5.00 g, 19.6 mmol) was added acetic anhydride (9.2 ml, 98.0 mmol). After this mixture was cooled to -20° C., sulfuric acid (0.5 ml, 9.8 mmol) was added to the cooled mixture drop-wise, and the resulting mixture was stirred at the same temperature for 2 h. Then the reaction temperature was raised to room temperature, and the mixture was further stirred for 14 h. The reaction solution was basified with sodium carbonate solution, and extracted with ethyl acetate (50 ml) three times. After the solvent was distilled off in vacuo, the residue was purified by silica gel column chromatography to give AcFTAP (4.20 g, 14.1 mmol, 74%).

EXAMPLE 1

Synthesis of R-diastereoisomer of FTAP (Abbreviated as R-FTAP Hereinafter, Formula IV-R) From Racemic FTAP

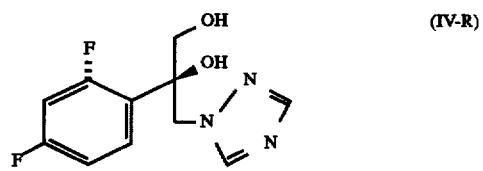
(IV-R)

Into a 21-mm diameter test tube equipped with a screw cap were placed a lipase (10 mg each) listed in Table 1, racemic FTAP (15 mg) and vinyl acetate (1 ml), and the mixture was shaken at 30° C. for 17 h. After the reaction was over, the lipase was separated by centrifugation, and the solvent was removed in vacuo. The residue thus obtained was dissolved in a solvent (hexane/ethanol=1/1), and subjected to high performance liquid chromatography using an optical resolution column [column: Chiralcel OD (Daicel Kagakukogyo), eluent: hexane/ethanol=15/1 containing 0.1% diethylamine, detection: UV 254 nm]. Yield and optical purity of the product was examined. Results are shown in Table 1.

TABLE 1

| Enzyme | Amount of enzyme added (mg) | FTAP | | | AcFTAP | | |
|---|---|---|---|---|---|---|---|
| | | Yield (%) | Optical purity (ee %) | Absolute configuration | Yield (%) | Optical purity (ee %) | Absolute configuration |
| Lipase M (from *Mucor javanicus*, Amanoseiyaku) | 60 | 60 | 33 | R | 40 | 72 | S |
| Lipase AY (from *Candida cylindracea*, Amanoseiyaku) | 10 | 37 | 43 | R | 63 | 30 | S |
| Penicillin lipase C (from *Penicillium cyclobium*, Cosmobio) | 3 | 11 | 51 | R | 89 | 7 | S |
| Lipase P (from *Pseudomonas sp.*, Nagase-Seikagakukogyo) | 10 | 53 | 14 | R | 47 | 19 | S |
| Lipase (from *Rhizopus delemar*, Seikagakukogyo) | 10 | 85 | 11 | R | 15 | 76 | S |
| Lipase SE-B (from *Pseudomonas fragi*, Funakosi) | 10 | 69 | 33 | R | 31 | 89 | S |
| Lipozyme ZM60 (from *Mucor miehei*, Novo) | 10 | 65 | 14 | R | 35 | 32 | S |
| LP10-071 (lipase purified from the culture medium of *Pseudomonas sp.* FERMP-12575) | 10 | 31 | 99 | R | 69 | 54 | S |
| LP16-019B (lipase purified from the culture medium of *Pseudomonas cepacia* FERMP-12574) | 40 | 28 | 78 | R | 72 | 39 | S |

EXAMPLE 2

Synthesis of R-diastereoisomer of AcFTAP (Abbreviated as R-AcFTAP Hereinafter, Formula III-R) From Racemic FTAP

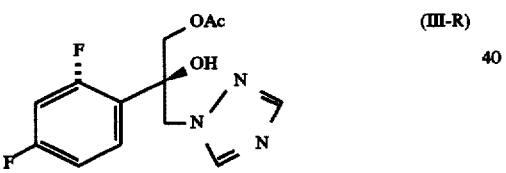

(III-R)

Into a 21-mm diameter test tube equipped with a screw cap were placed the lipase listed in Table 2 (10 mg each), racemic FTAP (15 mg) and vinyl acetate (1 ml), and the mixture was shaken at 30° C. for 17 h. After the reaction was over, the lipase was separated by centrifugation, and the solvent was removed in vacuo. The product was dissolved in a solvent (hexane/ethanol=1/1), and subjected to high performance liquid chromatography using an optical resolution column [column: Chiralcel OD (Daicelkagakukogyo), eluent hexane/ethanol=15/1 containing 0.1% diethylamine, detection: UV 254 nm]. Yield and optical purity of the product were determined. Results are shown in Table 2.

TABLE 2

| Enzyme | Amount of enzyme added (mg) | FTAP | | | AcFTAP | | |
|---|---|---|---|---|---|---|---|
| | | Yield (%) | Optical purity (ee %) | Absolute configuration | Yield (%) | Optical purity (ee %) | Absolute configuration |
| Zeotricium candida lipase (from *Geotrichum candidum*, Cosmobio) | 10 | 33 | 84 | S | 67 | 51 | R |

EXAMPLE 3

Synthesis of R-diastereoisomer of FTAP From Racemic AcFTAP

In a 21-mm test tube equipped with a screw cap, racemic AcFTAP (22.5 mg) synthesized according to Citation 1 was incubated with a lipase (10 mg each) listed in Table 3 in 100 mM phosphate buffer (pH 7.0) at 30° C. for 24 h. After the reaction was over, ethanol (4 ml) was added to the reaction mixture, and the enzyme was separated by centrifugation. After the solvent was removed, the product was dissolved in hexane/ethanol=1/1, and subjected to high performance liquid chromatography using an optical resolution column [column: Chiralcel OD [Daicel (Kagakukogyo), eluent: hexane/ethanol=15/1 containing 0.1% diethylamine, detection: UV254 nm]. Yield and optical purity of the product was determined. Results are shown in Table 3.

and subjected to high performance liquid chromatography [(column: Chiralcel OD (Daicel kagakukogyo), eluent: hexane/ethanol=15/1 containing 0.1% diethylamine, detection: UV 254 nm]. Yield and optical purity of the product were determined. Results are shown in Table 4.

TABLE 3

| | | FTAPT | | | AcFTAP | |
|---|---|---|---|---|---|---|
| Enzyme | Amount of enzyme added (mg) | Yield (%) | Optical purity (ee %) | Absolute configuration | Yield (%) | Optical purity (ee %) | Absolute configuration |
| Penicillin lipase R (from *Penicillium roquefortii*, Cosmobio) | 10 | 27 | 19 | R | 73 | 3 | S |
| Lipase OF (from *Candida cylindracea*, Meitosangyo) | 10 | 40 | 17 | R | 60 | 15 | S |

EXAMPLE 4

Synthesis of R-diastereoisomer of AcFTAP From Racemic AcFTAP

In a 21-diameter test tube equipped with a screw cap, racemic AcFTAP (22.5 mg) synthesized according to Citation 1 was incubated with a lipase (10 mg each) listed in Table 4 in the presence of 100 mM phosphate buffer (pH 7.0) at 30° C. for 24 h. After the reaction was over, ethanol (4 ml) was added to the reaction mixture, and the mixture was centrifuged to separate the enzyme. After the solvent was removed, the product was dissolved in hexane/ethanol=1/1,

TABLE 4

| | | FTAP | | | AcFTAP | | |
|---|---|---|---|---|---|---|---|
| Enzyme | Amount of enzyme added (mg) | Yield (%) | Optical purity (ee %) | Absolute configuration | Yield (%) | Optical purity (ee %) | Absolute configuration |
| Lipase M (from *Mucor javanicus*, Amanoseiyaku) | 10 | 13 | 52 | S | 87 | 14 | R |
| Penicillin lipase C (from *Penicillium cyclobium*, Cosmobio) | 10 | 85 | 7 | S | 15 | 48 | R |
| Lipase (from *Chromobacterium viscosum*, Asahikasei) | 10 | 28 | 61 | S | 72 | 35 | R |
| Rhilipase (from *Rhizopus japonicus*, Nagase-Seikagakukogyo) | 10 | 25 | 58 | S | 75 | 27 | R |
| Talipase (from *Rhizopus delemar*, Tanabeseiyaku) | 10 | 21 | 26 | S | 79 | 10 | R |
| Lipase P (from *Pseudomonas* sp., Nagase-Seikagakukogyo) | 10 | 25 | 38 | S | 75 | 16 | R |
| Lipase PL (from *Alcaligenes* sp., Meitosangyo) | 10 | 58 | 12 | S | 42 | 41 | R |
| LP16-019B (lipase purified from the culture medium of *Pseudomonas cepacia* FERMP-12574) | 10 | 32 | 16 | S | 68 | 10 | R |

EXAMPLE 5

Synthesis of R-diastereoisomer of FTAP from R-diastereoisomer of AcFTAP

To R-AcFTAP (0.297 g, 1.0 mmol) was added a solution of 15% potassium hydroxide in methanol (3 ml), and the mixture was stirred at room temperature for 1 h. The reaction mixture was extracted with ethyl acetate. After the solvent was distilled off in vacuo, the residue was purified by silica gel column chromatography to give an R-diastereoisomer of FTAP [0.242 g (0.95 mmol), yield 95%].

EXAMPLE 6

Racemization of AcFTAP with Sulfuric Acid

In the following Examples 6 to 16, S-diastereoisomer of FTAP, one of the starting materials, was obtained by optical resolution column fractionation of (2,4-difluorophenyl)-3-(1H-1,2,4-triazol-1-yl)propane-1,2-diol (abbreviated as FTAP hereinafter) which was synthesized by the method described in TokkaiHei 5-9183. Another starting material, S-diastereoisomer of 1-acetoxy-2-(2,4-difluorophenyl)-3-(1H-1,2,4-triazol-1-yl)-2-propanol (abbreviated as AcFTAP hereinafter) was obtained by chemical acetylation of said S-diastereoisomer of FTAP.

In addition, in the following Examples 6 to 16, the optical purity of AcFTAP was measured using "Chiralcel OD" (Daicel Kagakukogyo) for the column, and "hexane/ethanol=15/1 containing 0.1% diethylamine" as eluent. The optical purity of FTAP was measured using "Chiralcel OG(Daicel Kagakukogyo)" as the column and "hexane/ethanol=9/1 ) as eluent.

To S-diastereoisomer of AcFTAP(94.5% ee, 0.297 g, 1.00 mmol/[α]$_D^{24}$ =+46.9 (c=1.0, MeOH) was added sulfuric acid (0.6 ml), and the mixture was stirred at room temperature for 6 h. The mixture was then basified with sodium carbonate solution, and extracted with ethyl acetate (30 ml×2). After the solution was dried over anhydrous sodium sulfate, the solvent was distilled off in vacuo to give yellow oily material (0.29 g). Purification of said oily material by silica gel column chromatography gave 0.262 g of AcFTAP (recovery 88%). To AcFTAP thus obtained was added a methanolic solution of potassium hydroxide (15%, 3 ml), and the mixture was stirred at room temperature for 1 h. The reaction mixture was condensed in vacuo, and then extracted with water and ethyl acetate. After the solvent was distilled off in vacuo, the residue was purified by silica gel column chromatography to give 0.209 g of FTAP (overall yield 82%, 5.8% ee).

EXAMPLE 7

Racemization of AcFTAP by Sulfuric Acid and Acetic Acid (Part 1).

To S-diastereoisomer of AcFTAP (94.5% ee, 0.297 g, 1.00 mmol) were added acetic acid (1.5 ml) and sulfuric acid (0.6 ml), the mixture was stirred at 80° C. for 3 h. The reaction mixture was basified with sodium carbonate solution, and extracted with ethyl acetate (30 ml×2). After the solution was dried over anhydrous sodium sulfate, the solvent was distilled off in vacuo to give 0.27 g of yellow oily material. Purification of this oily material by silica gel column. chromatography gave 0.253 g of AcFTAP (recovery 85%, 0% ee). In a similar manner as described in Example 6, AcFTAP thus obtained was deacetylated by a methanolic solution of potassium hydroxide and then purified by silica gel column chromatography to give 0.206 g of FTAP (overall yield 81%, 0% ee).

EXAMPLE 8

Racemization of AcFTAP with Sulfuric Acid and Acetic Acid (Part 2)

AcFTAP (0.500 g, 1.68 mmol, 0% ee) which had been synthesized by the same method as used in Example 7 was dissolved in methanol (2.5 ml) and water (2.5 ml). To this solution was added sulfuric acid (2.5 ml), and the mixture was stirred at room temperature for 18 h, then at 80° C. for 3 h. The reaction mixture was basified with sodium hydroxide solution, and then extracted with ethyl acetate. After the solution was dried over anhydrous sodium sulfate, the solvent was removed in vacuo. The residue thus obtained was purified by silica gel column chromatography to give 0.388 g of FTAP (yield 90%, 0% ee).

EXAMPLE 9

Racemization of AcFTAP with Sulfuric Acid and Acetic Acid (Part 3)

To S-diastereoisomer of AcFTAP (94.5% ee, 0.500 g, 1.68 mmol) were added acetic acid (2.5 ml) and sulfuric acid (1.0 ml), and the mixture was stirred at 80° C. for 1 h. After the reaction mixture was basified with sodium carbonate solution, the mixture was extracted with ethyl acetate (50 ml×2). After the solution was dried over anhydrous sodium sulfate, the solvent was distilled off in vacuo to give 0.52 g of yellow oily material. Purification of this oily material by silica gel column chromatography gave 0.485 g (yield 97%) of AcFTAP with optical purity of 22.2% ee.

EXAMPLE 10

Racemization of AcFTAP with Trifluoromethanesulfonic Acid and Acetic Acid

To S-diastereoisomer of AcFTAP (S-AcFTAP) (94.5% ee, 0.297 g, 1.00 mmol) were added acetic acid (1.5 ml) and trifluoromethanesulfonic acid (0.6 ml), and the mixture was stirred at 80° C. for 3 h. After the reaction mixture was basified with sodium carbonate solution, it was extracted with ethyl acetate (30 ml×2). After the solution was dried over anhydrous sodium sulfate, the solvent was distilled off in vacuo to give 0.26 g of yellow oily material. Purification of this oily material by silica gel column chromatography gave 0.089 g (recovery 30%) of AcFTAP with optical purity of 39.2% ee.

EXAMPLE 11

Racemization of AcFTAP with Methanesulfonic Acid and Acetic Acid

To S-diastereoisomer of AcFTAP (94.5% ee, 0.297 g, 1.00 mmol) were added acetic acid (1.5 ml) and methanesulfonic acid (0.6 ml), and the mixture was stirred at 80° C. for 3 h. After the reaction mixture was basified with sodium carbonate solution, the mixture was extracted with ethyl acetate (30 ml×2). After the solution was dried over anhydrous sodium sulfate, the solvent was distilled off in vacuo to give 0.27 g of yellow oily material. Purification of this oily material by silica gel column chromatography gave 0.241 g (recovery 81%) of AcFTAP with optical purity of 83.4% ee.

EXAMPLE 12

Racemization of AcFTAP with 60% Perchloric Acid Solution and Acetic Acid

To S-diastereoisomer of AcFTAP (94.5% ee, 0.297 g, 1.00 mmol) were added acetic acid (1.5 ml) and 60% perchloric acid solution (0.6 ml), and the mixture was stirred at 80° C. for 20 h. After the reaction mixture was basified with sodium carbonate solution, the resulting mixture was extracted with ethyl acetate (30 ml×2). After the solution was dried over anhydrous sodium sulfate, the solvent was distilled off in vacuo to give 0.26 g of yellow oily material. Purification of this oily material by silica gel column chromatography gave 0.186 g (recovery 63%) of AcFTAP and 0.060 g (recovery 24%) of FTAP. AcFTAP and FTAP were combined, deacetylated with methanolic solution of potassium hydroxide in a similar manner as described in Citation 1, and purified by silica gel column chromatography to give 0.200 g of FTAP (overall yield 78%, 75.8% ee).

EXAMPLE 13

Racemization of AcFTAP with Sulfuric Acid and Ethyl Acetate

To S-diastereoisomer of AcFTAP (94.5% ee, 0.300 g, 1.01 mmol) were added ethyl acetate (1.5 ml) and sulfuric acid (0.6 ml), and the mixture was stirred at 80° C. for 20 h. After the reaction mixture was basified with sodium carbonate solution, the resulting mixture was extracted with ethyl acetate (30 ml×2). After the solution was dried over anhydrous sodium sulfate, the solvent was distilled off in vacuo to give 0.30 g of yellow oily material. Purification of this oily material by silica gel column chromatography gave 0.132 g (recovery 44%) of AcFTAP with optical purity of 0% ee.

EXAMPLE 14

Racemization of AcFTAP with Sulfuric Acid and Formic Acid

To S-diastereoisomer of AcFTAP (94.5% ee, 0.297 g, 1.00 mmol) were added formic acid (1.5 ml) and sulfuric acid (0.6 ml), and the mixture was stirred at 80° C. for 3 h. After the reaction mixture was basified with sodium carbonate solution, the resulting mixture was extracted with ethyl acetate (30 ml×2). After the solution was dried over anhydrous sodium sulfate, the solvent was distilled off in vacuo to give 0.23 g of yellow oily material. Purification of this oily material by silica gel column chromatography gave 0.088 g (recovery 31%) of 1-formyl-2-(2,4-difluorophenyl)-3-(1H-1,2,4-triazol-1-yl)-2-propanol, and 0.128 g (recovery 50%) of 2-(2,4-difluorophenyl)-3-(1H-1,2,4-triazol-1-yl)propane-1,2-diol. The two compounds thus obtained were combined, and to this mixture were added 10% sodium hydroxide solution (10 ml) and ethanol (10 ml). The resulting mixture was stirred at room temperature for 20 h. After the ethanol was distilled off in vacuo, the residue was extracted with ethyl acetate and water. The organic layer was condensed, and then purified by silica gel column chromatography to give 0.166 g (yield 65%) of FTAP with 7.6% ee.

EXAMPLE 15

Racemization of FTAP with Sulfuric Acid and Acetic Acid

To S-diastereoisomer of FTAP (94.5% ee, 0.500 g, 1.96 mmol) were added acetic acid (2.5 ml) and sulfuric acid (1.0 ml), and the mixture was stirred at 80° C. for 3 h. After the reaction mixture was basified with sodium carbonate solution, the resulting mixture was extracted with ethyl acetate (30 ml×2). After the solution was dried over sodium sulfate, the solvent was distilled off in vacuo to give 0.26 g of yellow oily material. Purification of this oily material by silica gel column chromatography gave 0.390 g (yield 78%) of AcFTAP with optical purity of 12.5% ee, and also 0.023 g (recovery 5%) of FTAP with optical purity of 83.6% ee.

EXAMPLE 16

Racemization of FTAP with Sulfuric Acid and Acetic Anhydride

To S-diastereoisomer of FTAP (94.5% ee, 5.10 g, 20.0 mmol) were added acetic anhydride (10.0 g) and further sulfuric acid (1.06 ml) at room temperature, and the mixture was stirred at 50° C. for 3 h, and then at 60° C. for 3h. After the reaction mixture was basified with sodium carbonate solution, the resulting mixture was extracted with ethyl acetate (30 ml×2). After the extract was dried over anhydrous sodium sulfate, the solvent was distilled off in vacuo to give 5.26 g of yellow oily material. Purification of this oily material by silica gel column chromatography gave 4.47 g (recovery 66%) of 1,2-diacetoxy-2-(2,4-difluorophenyl)-3-(1H-1,2,4-triazol-1-yl)propane with optical purity of 69.8% ee. To this compound was added a methanolic solution of potassium hydroxide (15%, 65 ml), and the mixture was stirred at room temperature for 20 h. After the methanol was distilled off from the reaction mixture in vacuo, the residue was extracted with water and ethyl acetate. The organic layer was condensed and purified by silica gel column chromatography to give 3.08 g (overall yield 60%, 69.8% ee) of FTAP. Optical purity of said 1,2-diacetoxy-2-(2,4-difluorophenyl)-3-(1H-1,2,4-triazol-1-yl)propane was measured in a similar manner as described for that of said AcFTAP.

INDUSTRIAL APPLICABILITY

By the present invention, economic and convenient synthesis of a compound having the formula (II-R) has become possible. Furthermore, this invention provides a method for preparing a compound having the formula (I-R) which is utilized for the synthesis of a compound having the formula (II-R).

What is claimed is:

1. A process for producing a compound having the formula (II-R), said process comprising the steps of (a) providing a compound having the formula (II), a compound having the formula $R_1COOR_2$, and a microbial lipase; and (b) enzymatically reacting said compound having the formula (II) with said compound having the formula $R_1COOR_2$, in the presence of said microbial lipase, under conditions permitting formation of a compound having the formula (II-R);

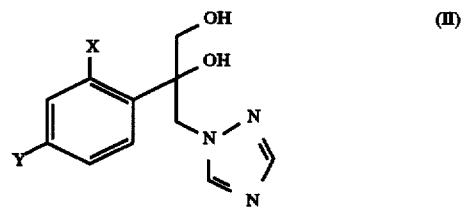

(II)

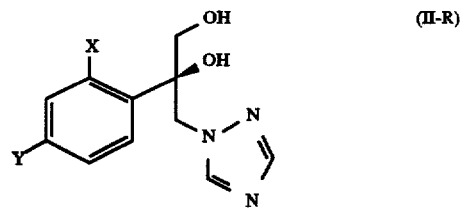

(II-R)

wherein X and Y are either halogen or hydrogen atoms, wherein X and Y may be the same or different atoms;

wherein the configuration of the asymmetric carbon is R; and wherein $R_1$ is a straight or branched $C_1$ to $C_4$ alkyl or alkenyl group, and $R_2$ is a straight or branched $C_1$ to $C_6$ alkyl or alkenyl group.

2. The process according to claim 1, wherein said lipase is derived from a microorganism belonging to the genus Mucor, Candida, Penicillium, Pseudomonas or Rhizopus.

3. The process according to claim 1, wherein said lipase is derived from *Pseudomonas sp* FERMP-12575.

4. A process for producing a compound having the formula (I-R), said process comprising the steps of (a) providing a compound having the formula (II), a compound having the formula $R_1COOR_2$, and a microbial lipase; and (b) enzymatically reacting said compound having the formula (II) with said compound having the formula $R_1COOR_2$, in the presence of said microbial lipase, under conditions permitting formation of a compound having the formula (I-R);

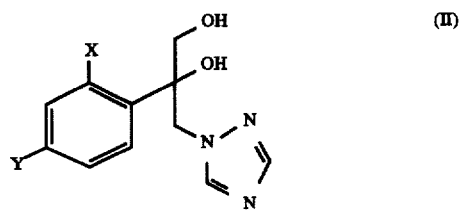
(II)

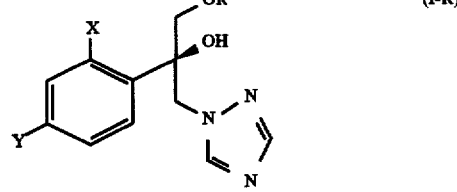
(I-R)

wherein X and Y are halogen or hydrogen atoms; wherein X and Y may be the same or different atoms;
wherein the configuration of the asymmetric carbon is R; and
wherein $R_1$ is a straight or branched $C_1$ to $C_4$ alkyl or alkenyl group, $R_2$ is a straight or branched $C_1$ to $C_6$ alkyl or alkenyl group, and R is $COR_1$.

5. The process according to claim 4, wherein said lipase is derived from microorganism belonging to the genus Geotricum.

6. A process for producing a compound having the formula (II-R), said process comprising the steps of (a) providing a compound having the formula (I) and a microbial lipase; and (b) hydrolyzing said compound having the formula (I) in the presence of said microbial lipase, under conditions permitting formation of a compound having the formula (II-R);

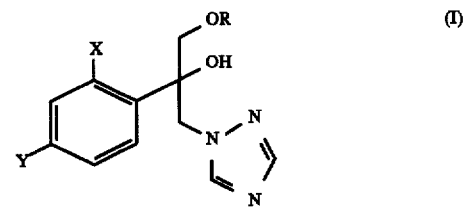
(I)

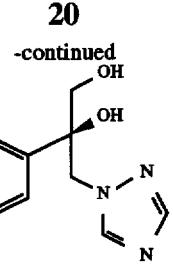
(II-R)

wherein X and Y are halogen or hydrogen atoms;
wherein X and Y may be the same or different atoms;
wherein the configuration of the asymmetric carbon is R; and
wherein R is $COR_1$, wherein $R_1$ is a straight or branched $C_1$ to $C_4$ alkyl or alkenyl group.

7. The process according to claim 6, wherein said lipase is derived from a microorganism belonging to the genus Penicillium or Candida.

8. A process for producing a compound having the formula (I-R), said process comprising the steps of (a) providing a compound having the formula (I) and a microbial lipase; and (b) hydrolyzing said compound having the formula (I) in the presence of said microbial lipase, under conditions permitting formation of a compound having the formula (I-R);

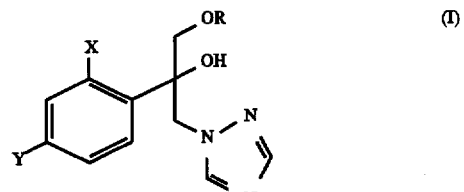
(I)

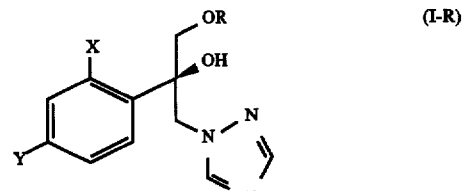
(I-R)

wherein X and Y are halogen or hydrogen atoms;
wherein X and Y may be the same or different atoms;
wherein the configuration of the asymmetric carbon is R;
and wherein R is $COR_1$, wherein $R_1$ is a straight or branched $C_1$ to $C_4$ alkyl or alkenyl group.

9. The process according to claim 8, wherein said lipase is derived from a microorganism belonging to the genus Mucor, Penicillium, Chromobacterium, Rhizopus, Pseudomonas or Alcaligenes.

10. The process according to claims 1, 4, 6 or 8, wherein both X and Y are fluorine atoms.

11. The process according to claims 1, 4, 6 or 8, wherein $R_1$ is methyl group.

12. The process according to any one of claims 1 or 4, wherein $R_2$ is a vinyl group.

13. The process according to claims 1, 4, 6 or 8, wherein both X and Y are fluorine atoms, and where $R_1$ is methyl group.

14. The process according to claims 1 or 4, wherein both X and Y are fluorine atoms, where $R_1$ is methyl group, where $R_2$ is vinyl group.

15. The process according to claim 1, wherein lipase is derived from microorganism belonging to the genus Mucor, Candida, Penicillium, Pseudomonas or Rhizopus, or animals, where both X and Y are fluorine atoms, where R1 is methyl group.

16. The process according to claim 1, wherein lipase is derived from microorganism belonging to the genus Mucor, Candid, Penicillium, Pseudomonas or Rhizopus, or animals, where both X and Y are fluorine atoms, where $R_1$ is methyl group, where $R_2$ is vinyl group.

17. The process according to claim 4, wherein lipase is derived from microorganism belonging to genus Geotrichum, where both X and Y are fluorine atoms, where $R_1$ is methyl group.

18. The process according to claim 9, wherein lipase is derived from microorganism belonging to genus Geotrichum, where both X and Y are fluorine atoms, where $R_1$ is methyl group, where $R_2$ is vinyl group.

19. The process according to claim 6, wherein lipase is derived from microorganism belonging to the genus Pencillium or Candid, where both X and Y are fluorine atoms, where $R_1$ is methyl group.

20. The process according to claim 8, wherein lipase is derived from microorganism belonging to the genus Mucor, Penicillium, Chromobacterium, Rhizopus, Pseudomonas, or Alcaligenes, where both X and Y are fluorine, where $R_1$ is methyl group.

21. A process for producing a compound having the formula (II) comprising reducing or eliminating the optical activity of a compound having the formula (I-R) or (I-S) by treatment with a strong acid followed by deacylation;

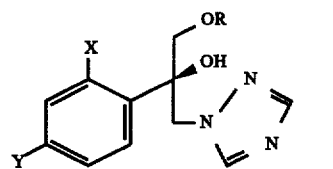
(I-R)

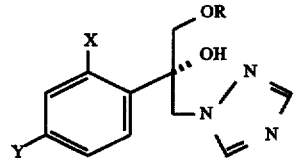
(I-S)

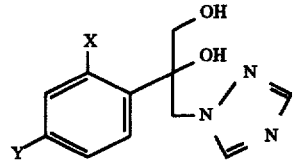
(II)

wherein X and Y are halogen or hydrogen atoms; wherein X and Y may be the same or different atoms; and wherein R is $COR_1$, wherein $R_1$ is a hydrogen atom, or a straight or branched alkyl, alkenyl, aryl or aralkyl groups.

22. The process according to claim 21 wherein $R_1$ is hydrogen atom, or straight or branched alkyl group.

23. The process according to any one of claim 22, wherein $R_1$ is a methyl group.

24. The process according to claims 21 to 23, wherein both X and Y are fluorine atoms.

25. The process according to claim 21, wherein the reaction is performed in the presence of an acylating agent.

26. A process for producing a compound having the formula (II) comprising reducing or eliminating the optical activity of a compound having the formula (II-R) or (II-S) by treatment with a strong acid in the presence of an acylating agent followed by deacylation;

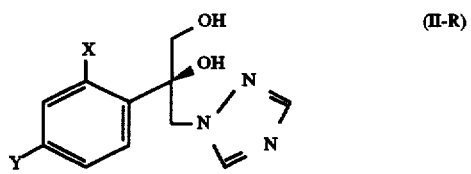
(II-R)

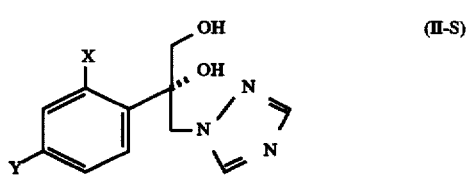
(II-S)

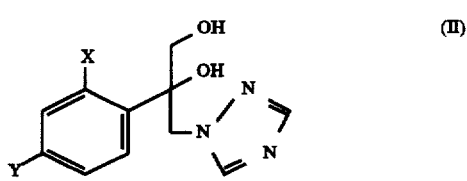
(II)

wherein X and Y are halogen or hydrogen atoms; wherein X and Y may be the same or different atoms.

27. The process according to claim 26, wherein both X and Y are fluorine atoms.

28. The process according to claims 26 or 27, wherein said acylating agent is aliphatic carboxylic acid.

29. The process according to claim 28, wherein said acylating agent is acetic acid.

30. The process according to claim 28, wherein said acylating agent is formic acid.

31. The process according to any one of claims 21–23, 25–27, 29 or 30, wherein said strong acid is sulfuric acid.

* * * * *